United States Patent [19]
Carrabba et al.

[11] Patent Number: 5,112,127
[45] Date of Patent: May 12, 1992

[54] APPARATUS FOR MEASURING RAMAN SPECTRA OVER OPTICAL FIBERS

[75] Inventors: Michael M. Carrabba, Franklin; R. David Rauh, Newton, both of Mass.

[73] Assignee: EIC Laboratories, Inc., Norwood, Mass.

[21] Appl. No.: 442,235

[22] Filed: Nov. 28, 1989

[51] Int. Cl.$^5$ ............................................. G01J 3/44
[52] U.S. Cl. .............................. 356/301; 250/227.23
[58] Field of Search ............... 356/301, 317, 318, 300; 250/237 R, 227.18, 227.23

[56] References Cited

U.S. PATENT DOCUMENTS

| | | | |
|---|---|---|---|
| 4,164,651 | 8/1979 | Oikawa | 250/237 R |
| 4,573,761 | 3/1986 | McLachlan et al. | 350/96.24 |
| 4,781,458 | 11/1988 | Angel et al. | 356/301 |
| 4,802,761 | 2/1989 | Bowen | 356/301 |

FOREIGN PATENT DOCUMENTS

2530024  1/1984  France ................................. 356/301

OTHER PUBLICATIONS

The Utilization of a Holographic Bragg Diffraction Filter for Rayleigh Line Rejection in Raman Spectroscopy-Carrabba et al-Applied Spectroscopy-vol. 44, #9, 1990.
D. D. Archibald et al., "Raman Spectroscopy Over Optical Fibers with the Use of a Near-IR FT Spectrometer", Appl. Spectroscopy 1984, 42, 1558–1563.
M. M. Carrabba et al., "The Suitability of Surface Enhanced Raman Spectroscopy (SERS) to Fiber Optic Chemical Sensing of Aromatic Hydrocarbon Contamination in Groundwater", in first Int. Symp. on Field Screening Methods for Hazardous Waste Site Investigations, Oct. 11–13, 1988, pp. 31–40.
P. J. Hendra, G. Ellis and D. J. Cutler, "Use of Optical Fibers in Raman Spectroscopy", 1988, 19, 413–418.
P. Plaza, N. Quy Dao, M. Jouan, H. Fevrier and H. Saisse, "Simulation et Optimisation des Capteurs a Fibres Optiques Adjacentes", Applied Optics, Oct. 1986, 25, 3448–3454.
S. D. Schwab, R. McCreery and F. T. Gamble, "Normal and Resonance Raman Spectroelectrochemistry with Fiber Optic Light Collection", Anal. Chem., 1986, 58, 2486.
H. Yamada and Y. Yamamoto, "Illumination of Flat or Unstable Samples for Raman Measurements using Optical Fibres", J. Raman Spectroscopy, 1980, 9, 401–402.

*Primary Examiner*—Vincent P. McGraw
*Assistant Examiner*—LaCharles P. Keesee

[57] ABSTRACT

A fiber-optic probe which is useful for measuring Raman spectra of samples remote from the light source and detector. The probe head contains optical components which selectively remove unwanted fluorescence and Raman scattering arising from the interaction between the Raman excitation source radiation and the input optical fiber. The optics also filter the Raman excitation source into a return optical fiber leading to a spectrometer or detector. In one embodiment, the disposition of optical components provides a compact probe geometry with parallel input and output fibers at one end and a sampling port at the other end. An encasement for the optics is also disclosed, for sealing the components against the environment, and for coupling the probe to specialized sampling attachments, such as for conducting Surface Enhanced Raman Spectroscopy.

13 Claims, 5 Drawing Sheets

APPARATUS FOR MEASURING RAMAN SPECTRA OVER OPTICAL FIBERS

This invention was made with Government support under Contract No. N00014-88-C-0661 awarded by the U.S. Office of Naval Research.

FIELD OF THE INVENTION

This invention relates to instrumentation for conducting Raman spectroscopy in analytes remote from the generating light source and signal processing apparatus using optical fibers.

Vibrational spectroscopy has long been a useful technique for characterizing molecules and for determining their chemical structure. The vibrational spectrum of a molecule typically consists of a series of sharp lines which constitute a unique fingerprint of the specific molecular structure. There are various instances where it would be desirable to measure the vibrational spectrum of a sample in a remote or hostile environment. To measure spectroscopic absorption over optical fibers, light from a source is delivered to sample over one fiber and the light after passage through the sample is collected by another fiber. The collected light is directed back to an instrument for analyzing its wavelength and/or intensity, such as a monochrometer and a photodetector. However, silica or plastic optical fibers themselves absorb in the 2 to 50 $\mu m$ wavelength region, and so cannot be used for remote measurements of absorption in the infrared spectral region where molecular vibrational transitions occur.

Raman spectroscopy presents a means of obtaining vibrational spectra over optical fibers with visible or near infrared light. These wavelength regions are efficiently transferred without significant absorption losses over conventional optical fiber materials. In Raman spectroscopy, monochromatic light is directed onto a sample and the spectrum of the scattered light is determined. In a typical Raman experiment, the excitation light source is a single laser line, such as the 514.5 nm (19435 $cm^{-1}$) line from an Argon ion gas laser. Most of the light scattered off the sample will also be at this wavelength (the Rayleigh line), but approximately 1 part in $10^6$ will be scattered at wavelengths containing the sum or difference of the Rayleigh and molecular vibrational frequencies. For example, if a molecule has a Raman active vibration at 10 $\mu m$ (1000 $cm^{-1}$), the a line will appear in the scattered light spectrum at 20436 $cm^{-1}$ (489 nm). This very weak signal means that the excitation light must be quite intense. In addition, optical filtering is necessary to separate the weak scattered signal from the intense Rayleigh line.

Obtaining Raman spectra over long distances of optical fibers has a major problem. Sending intense laser light through long segments of optical fiber gives rise to spurious optical signals that can interfere with the spectroscopic measurements. Stimulated Raman Scattering in optical fibers is a well-known problematic phenomenon in optical communications, see for example G. P. Agrawal, *Nonlinear Fiber Optics*, Ch. 8, Academic Press, New York, 1989. These signals originate both from the fluorescence and Raman scattering arising from impurities in the fiber core and cladding and can hide the Raman spectrum of the sample being monitored. Similarly, unless the intense Rayleigh line is removed before the scattered light enters the collection fiber, it is likely to be of sufficient intensity to excite Raman scattering or fluorescence in the collection fiber as well, thus interfering with the desired spectral signals. Both of these problems require that the optics for filtering the exciting and scattered light be placed at the sampling end of the optical fibers.

Prior art describes apparatus and optical fiber configurations for conducting remote Raman spectroscopy, see for example McLachlan, et al., U.S. Pat. No. 4,573,761. None of the prior art deals with the problem of removing the spurious optical signals originating in the excitation and collection fibers.

The present invention solves the problem of removing unwanted optical interference originating in the excitation and collection fibers of a remote fiber optic Raman spectrometer and also provides a convenient sampling head assembly for addressing liquid, solid and gaseous samples. Important uses for the probe include environmental monitoring of organic contaminants in water supplies, process monitoring in vats for chemical synthesis and fermentation, monitoring of distillate distribution in distillation columns, monitoring of chemical fluxes in chemical vapor deposition reactors, and on-line monitors for various types of chromatographic separation. The probe is generally useful as a convenient sampling arrangement for Raman spectroscopy in any application.

SUMMARY OF THE INVENTION

The invention describes an optical probe for use in remote Raman spectroscopy. The probe is used as a component in instrumentation comprising 1) a light source, such as a laser which is coupled to an optical fiber or fiber bundle for the low-loss transmission of the light to the probe, which is placed in contact with the sample to be measured, and 2) a return fiber or fiber bundle exiting the probe which returns the light scattered from the sample to a spectroscopic analyzing instrument such as a spectrometer. The probe disclosed in this invention consists of 1) optics for filtering the excitation light, thus removing interfering Raman scattering and fluorescence arising from the exciting fiber; 2) optics for focusing the exciting light onto a sample external from the probe; 3) optics for collecting the scattered light from the sample and removing the intense laser excitation line from the desired spectral features; 4) optics for refocusing the scattered light for acceptance by the exit fiber or fiber bundle. An enclosure, ideally sealed from the environment, containing the optical components, is also a feature of the invention.

DETAILED DESCRIPTION OF THE INVENTION

Figure 1:
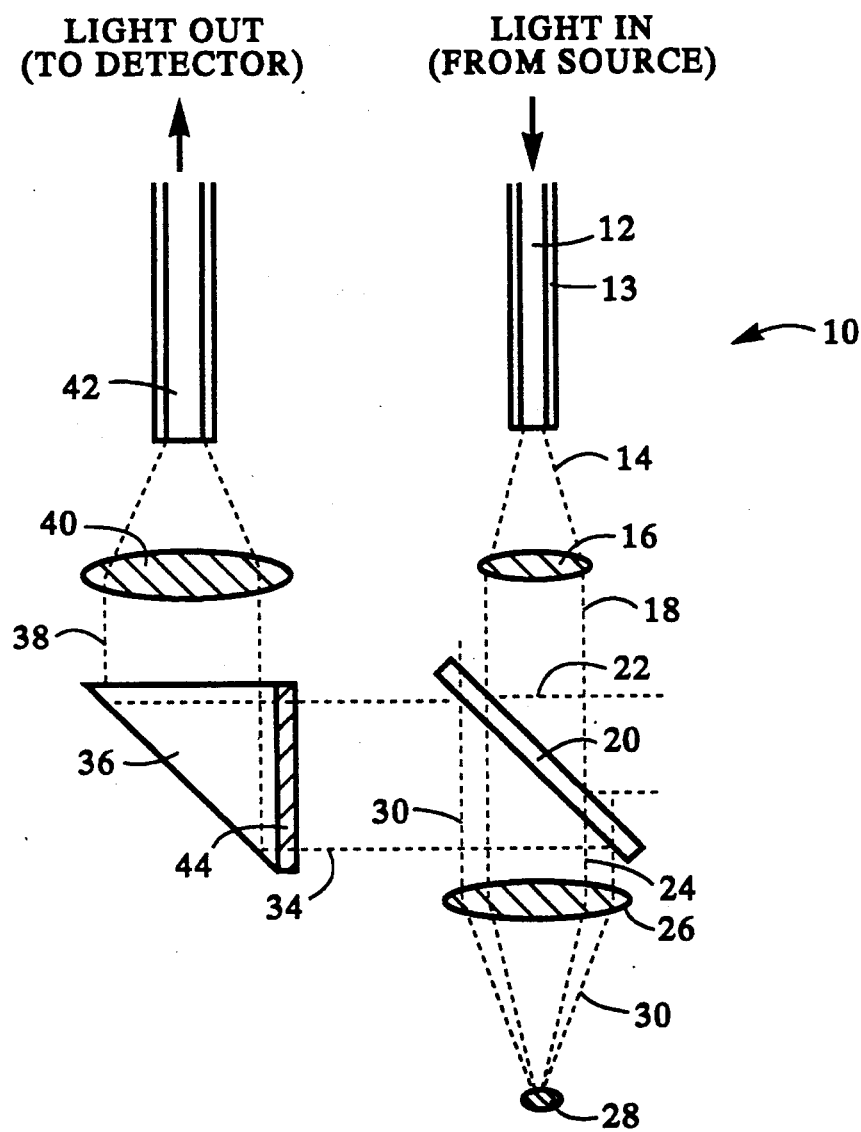
FIG. 1 is a schematic view of the preferred embodiment of the Raman probe optics.

Referring first to FIG. 1 of the drawings is a schematic view of the optical components of a probe head 10 for conducting remote fiber optic Raman spectroscopy. Light from a remote excitation source, such as a laser, is conducted down the fiber core 12 with a cladding of lower index of refraction 13. The light 14 exiting the fiber is divergent, and is collimated (made parallel) by lens 16 (or an equivalent assembly of lenses). Lens 16 may be made of glass or plastic, and may be of traditional circular shape or may be a graded index lens (GRIN lens) of cylindrical geometry. Lenses of small dimensions are preferred to minimize the overall size of the probe.

After collimation, the light 18 is passed through an optical filter 20 at an angle of approximately 45° with respect to the light path. In the preferred embodiment, the filter has the property of passing light within a narrow band of wavelengths and rejecting other wavelengths by reflection. The filter is specifically chosen to pass the laser excitation wavelength at the 45° angle of incidence. The rejected light 22 contains any fluorescence or Raman scattering arising from within the excitation fiber. The filtered excitation light 24 next encounters a focusing lens or assembly of lenses 26 in the optical path. The emerging light is thus directed onto sample 28.

The light 30 scattered from the sample contains both the high intensity excitation source Rayleigh wavelength and the weaker Raman wavelengths. This light is collected by the same lens 26 used originally for focusing the collimated excitation light. In reverse, lens 26 collimates scattered light 30. The collimated beam next strikes the back side of filter 20, where again the intense light of the excitation wavelength passes straight through (beam 32). Thus, a requirement of filter 20 is that it reject light off of its back side by reflection. The light containing the Raman spectrum is reflected off filter 20 at approximately 90°. The Raman beam 34 next enters prism 36, where it is reflected off the back surface situated at an angle to direct the beam in a direction approximately 180° with respect to the input beam 18. The reflected beam 38 is then focused by lens or lens assembly 40 into the face of exit optical fiber 42, where it is returned to a detector or spectrometer. Prism 36 could be replaced by a mirror, but a prism is generally preferred because total internal reflection at the prism air interface is higher than most mirrors and is less susceptible to environmental fouling.

The above geometry is preferred because the input and output optical fibers are parallel. Thus, the fiber bundles are directed into one end of the probe, while the other end of the probe is placed in contact with the sample. However, it is possible to remove the prism 36 and to arrange lens 40 so that the return optical fiber is approximately 90° with respect to the input fiber.

Because of the high intensity of the scattered light at the exciting wavelength, it is desirable to place a second selective filter 44 in the beam path at the entrance to prism 36. In the preferred embodiment, this filter is a long wavelength passing edge filter, with a sharp cutoff of transmission of all wavelengths equal to and shorter than the excitation wavelength. This provides a second level of discrimination against the excitation light, since dichroic filter 20 is typically not 100% efficient. Alternatively, filter 44 may be replaced by a bandstop filter, which selectively absorbs or reflects back only the very narrow excitation wavelength, allowing all other wavelengths to pass. Filters having this characteristic include so-called Bragg filter, made from an oriented dispersion of monodispersed colloidal particles, and Rugate filters comprised of multiple layers of sinusoidally modulated refractive index. If only a narrow band of wavelengths is being monitored, filter 44 can be a selective bandpass filter.

Figure 2:
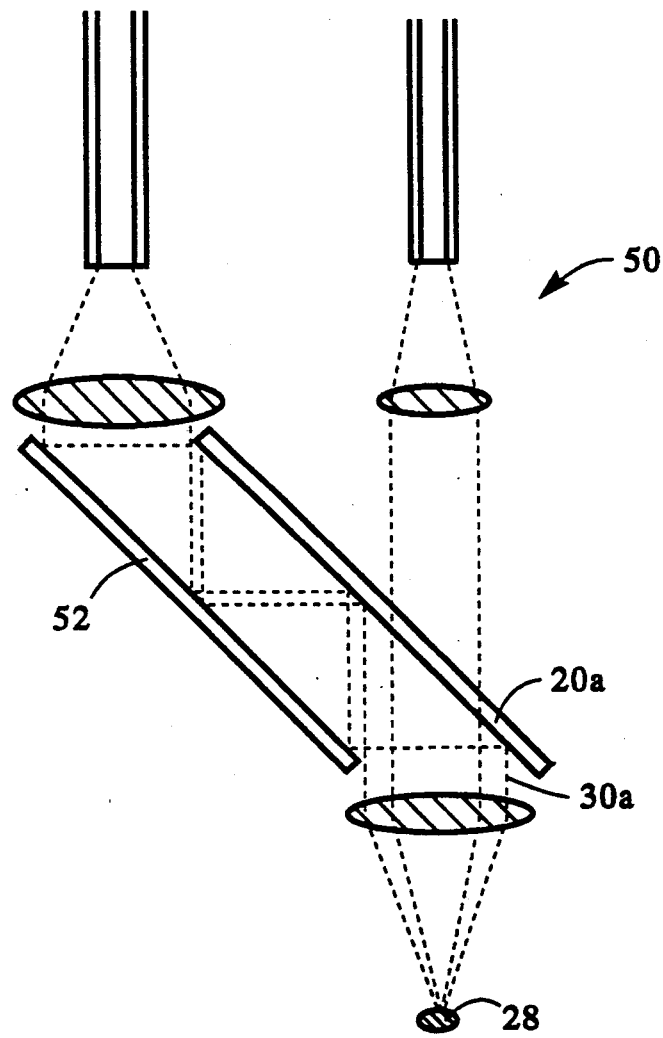
FIG. 2 is a schematic view of an alternative embodiment of the Raman probe incorporating two dichroic bandpass filters arranged for multiple internal reflections.

A principal objective of the invention is to provide a probe which efficiently removes spurious signals from the Raman spectrum before the spectrum is introduced into the return optical fiber 42. The optical elements responsible for isolating the Raman spectrum are filters 22 and 44. FIG. 2 shows an alternative embodiment 50 which may show improvements over the preferred embodiment in some applications. FIG. 2 shows a combination of two filters, 20a and 52, each tuned to pass the laser excitation wavelength at the angle of incidence and reflect other wavelengths. The second filter 52 replaces filter 44 and prism 36 (FIG. 1), and is separated from but in close spatial parallel arrangement with filter 20a. Filter 52 is also translated linearly with respect to 22a to permit entrance of collimated light beam 30a in one end of the separated pair; the beam is then multiply reflected between the two filters, each reflection giving rise to rejection of >90% of the remaining Rayleigh component. The linear shift in filter 52 finally enables the light beam to exit the filter pair after a final reflection off filter 52 and to be directed into the focusing optics at the desired angle of 180° from the direction of the excitation beam.

Other filtering optical elements may augment the dichroic bandpass filter element 20 when placed between lens 16 and filter 20. These may include bandpass filters which are made for use at normal incidence and which absorb or reflect nearly all but a narrow range of wavelengths or volume holograms, which disperse in back-reflection all but a narrow band of wavelengths tuned to the laser source, the latter being transmitted.

Figure 3:
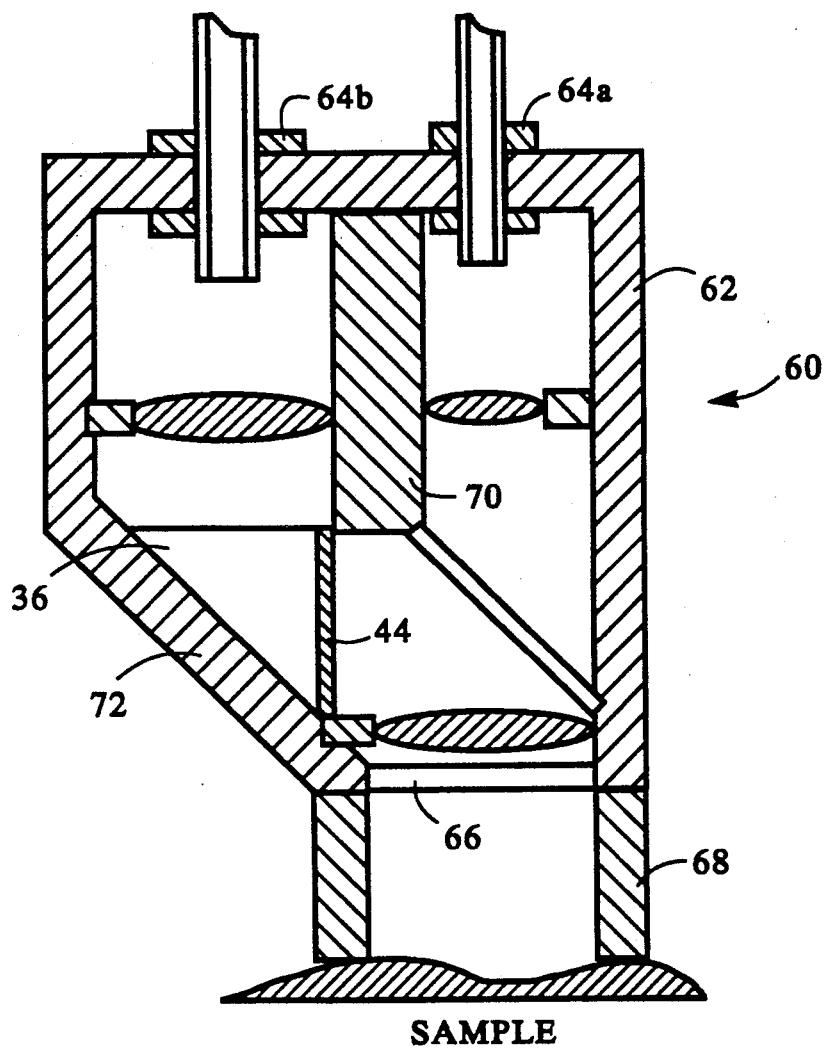
FIG. 3 is a sectional view of a typical probe encasement.

FIG. 3 shows the preferred embodiment of an encasement 60 used to contain the optics shown in FIG. 1 and to shield them from a potentially corrosive environment. Case 60 is preferably machined from a black, light absorbing polymer to minimize multiple internal reflections of scattered light. The case contains optical fiber feedthroughs, 64a and 64b, which serve the dual functions of providing a seal around the circumference of the incoming and outgoing fibers or fiber bundles, and also holding the fibers in a rigid optical configuration with respect to the internal optics. The other end of the case is sealed with an optical window, 66, through which the exciting light is focused onto the sample. Spacers 68 may be used to maintain an optimal distance between the window and a solid sample. Baffles such as 70 may be used to prevent scattered light from interfering with the spectrum either directly or through internal reflections within the case. An angled case wall, 72, is shown to provide convenient angular mounting of prism 36 as well as to narrow the probe end to enhance specificity of probe placement.

Figure 4:
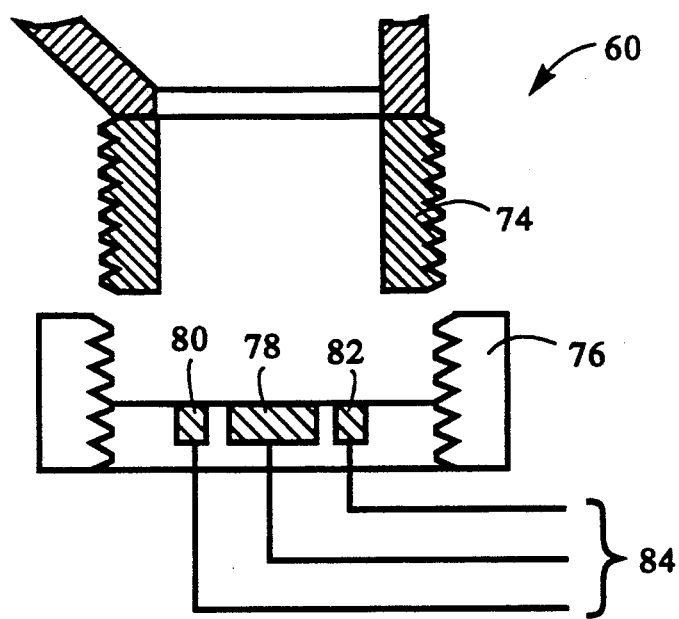
FIG. 4 shows schematically the attachment of accessories to a typical probe encasement: a) electrochemically regenerated substrate for Surface Enhanced Raman; b) auxiliary fiber optic coupler.
Figure 4:
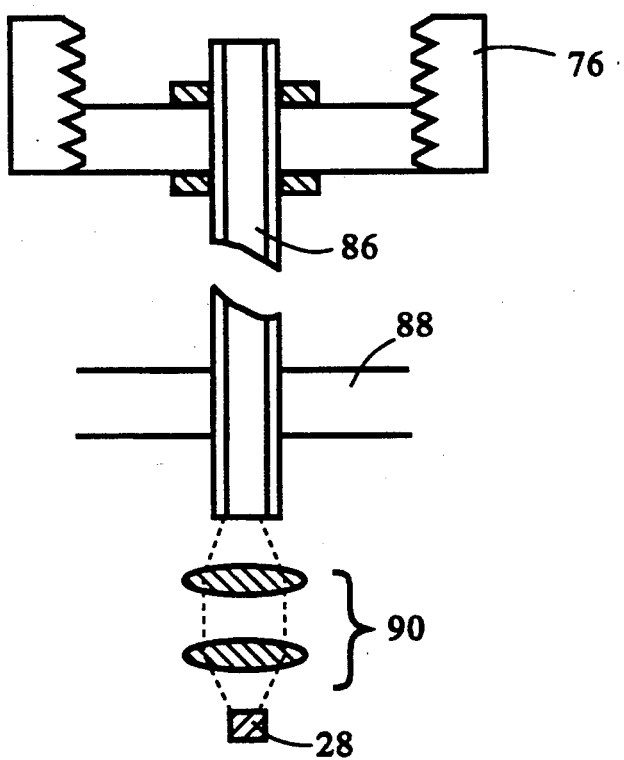

As shown in FIG. 4, an adaptor coupling, such as a threaded adaptor 74, can replace spacers 68 (FIG. 3) for convenient mounting of various sampling accessories. For example, the probe configuration is also useful in Surface Enhanced Raman Spectroscopy (SERS). In this technique, molecules adsorbed onto certain highly roughened metal surfaces have been seen to give rise to Raman spectra with up to $10^6$ enhancement in scattering intensity. Suitably rough metal surfaces (e.g., silver) may be prepared by high vacuum techniques, by casting colloidal dispersions of the metal onto a substrate, by photolithographic patterning, or by electrochemical roughening. FIG. 4a shows an addition of an electrochemical cell to the probe base for conducting SERS experiments. It consists of a threaded adaptor 76 mated to probe adaptor 74. Incorporated into the base of adaptor 76 are metal electrodes, including a SERS-active working electrode 78, and auxiliary reference and counter electrodes, 80 and 82. Electrical leads 84 are attached to the electrodes and join the electrodes to appropriate electrochemical control instrumentation. A similar attachment may be configured for gas phase sampling using SERS, in which adsorption/desorption of the gaseous species is controlled via an externally controllable heating element in contact with the SERS-active substrate.

The adaptor coupling can also be used to attach a secondary optical fiber, also shown in FIG. 4. For example, if a high temperature environment were being sampled, this could damage the probe optics, particularly the filters. Thus, a short segment of optical fiber 86 would extend from the probe head across a barrier 88 into the adverse environment where it would be focused by lens or lens assembly 90 onto the sample 28. The optical fibers connecting the light source and spectrometer to the probe would be much longer, and would give rise to the vase majority of spurious signal, which would be removed by the probe head.

EXAMPLE

Figure 5:
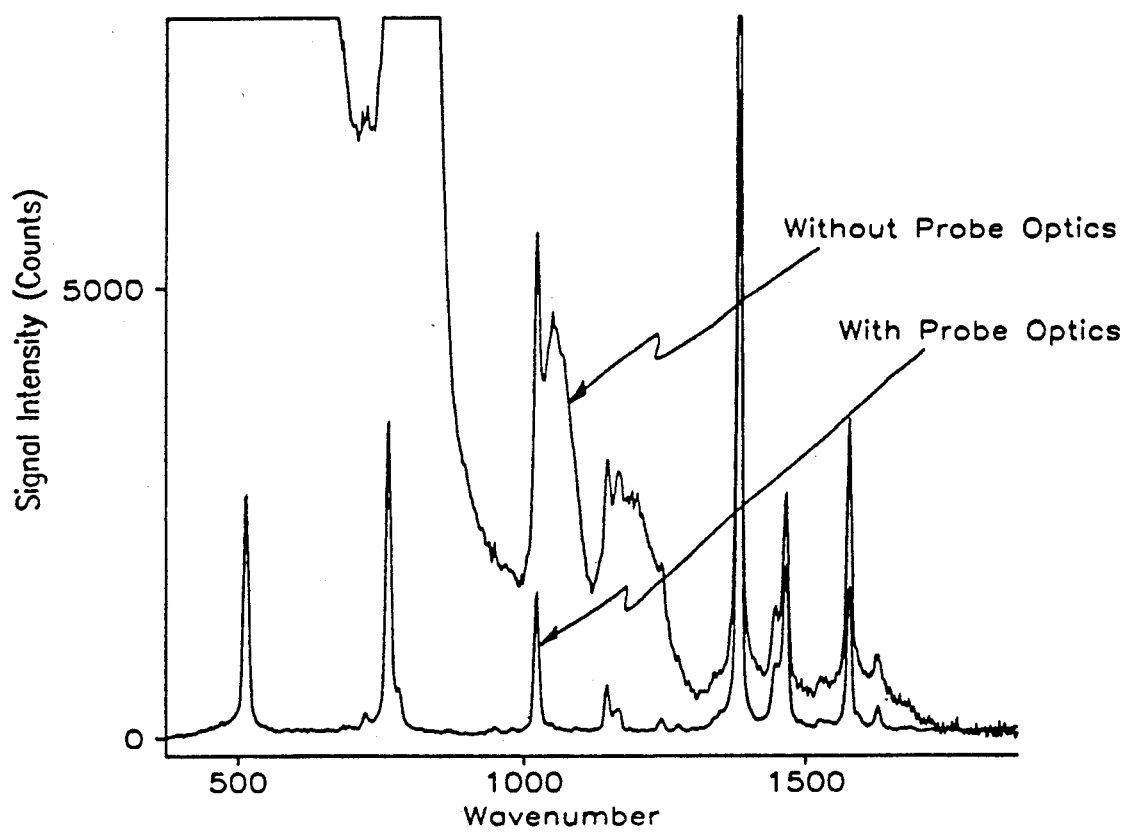
FIG. 5 shows the Raman spectra of solid naphthalene recorded over 50 meters of optical fiber a) without and b) with the probe in place.

The invention has been demonstrated in various embodiments. One example consist of the following. One hundred milliwatts of laser light at 514.5 nm exits 50 meters of an excitation fiber, a 50 $\mu$m core diameter fiber from Polymicro Technologies, Inc. (50/70/120), and is collimated by a GRIN lens (NSG America, Somerset, N.J.). The collimated light passed through an Omega Optical filter (550BP10) which is at a 45° angle. The filtered collimated light is then focused by Newport Corporation Lens (KPX010) onto a solid naphthalene sample. The scattered Raman light is then collected and collimated by the same KPX010 lens. The light is directed onto the back of the 55BP10 filter so that the Raman light is reflected 90° and the unwanted Rayleigh scattering is passed through the filter. The collimated Raman scattered light is then passed through another Omega Optical filter (530EFLP) to remove any remaining Rayleigh scattering. The twice filtered Raman light is then focused by a Newport Corporation KPX010 lens onto the collection fiber which is a 200 $\mu$m core diameter Polymicro technologies fiber optic (FHP) 200/240/270). The output from 50 meters of the collection fiber is then coupled to a Raman spectrometer. The spectrum obtained using the filtering arrangement is shown in FIG. 5. This is to be compared with the spectrum of the same sample recorded without the optical filter arrangement, also shown in FIG. 5. It can be seen in the latter case that the Raman spectrum of additional spurious components is superimposed on the naphthalene spectrum. These components arise from the optical fibers themselves and are efficiently removed by the filtering system.

The detailed specifications of the invention described above should not be construed as limitations of the scope of the invention, but rather as examples of preferred embodiments. Many other variations and modifications are possible within the scope of the following claims.

What is claimed is:

1. An optical probe useful for conducting Raman spectroscopy remotely over optical fibers with minimal interference from Raman scattering and or luminescence within said fibers comprising a first optical fiber transmissive at the wavelength used for Raman excitation for transmitting the Raman excitation light to the sample a probe head assembly of optical elements said assembly having the functions of delivering light from the end of said first optical fiber to the sample, of collecting Raman scattered light from the sample and of focusing said Raman scattering light into a second optical fiber said second optical fiber transmitting said Raman scattering light to a detector means for measuring the intensity and or spectral distribution of said Raman scattered light said probe head optical assembly also having the geometric configuration such that the input and output fibers are colinear and are connected to the proximal end of the probe and the sample is illuminated from the distal end of the probe head wherein said probe head assembly comprising a first lens or lens assembly spaced from the exit of said first optical fiber for collimating the light exiting said first optical fiber, followed in the optical path by a primary optical filter that is tuned to pass said Raman excitation wavelengths, but that is rejecting of light of other wavelengths generated within said first optical fiber by said excitation light said primary optical filter being arranged at approximately 45° with respect to the light path, followed in the optical path by a second lens or lens assembly for focusing the light said second lens or lens assembly directing the Raman excitation light onto the sample the scattered light from the sample being collected and collimated by the same second lens or lens assembly used for focusing the exciting light said collimated scattered light impinging onto the back face of said angled primary optical filter said primary filter admitting light of said Raman excitation wavelengths while reflecting the remaining light at approximately 90°, said remaining light containing the desired Raman spectrum, followed in the optical path by a second reflecting element inserted at approximately 45° with respect to the light path said second reflecting element reflecting the light at approximately 90° thus returning the light on a path approximately parallel, but in reverse direction to the input light, said second reflecting element being followed in the optical path by a third lens or lens assembly for focusing said reflected light into the end aperture of said second optical fiber or fiber bundle, approximately parallel to said first optical fiber or fiber bundle and transmissive at the wavelengths of the Raman scattered light said second optical fiber transmitting said Raman scattering light to a detector means for measuring the intensity and or spectral distribution of said Raman scattered light.

2. The optical probe of claim 1 further including a first supplementary filter which selectively blocks the excitation wavelength but passes the wavelength interval containing the desired Raman spectrum and is placed in the optical path between said angled primary filter and said second reflecting element, said additional filter further removing the excitation light from the scattered Raman spectrum.

3. The optical probe of claim 2 wherein said first supplementary filter is selected from the group comprising a Bragg filter, a holographic filter, a Rugate filter and a long wavelength passing edge filter.

4. The optical probe of claim 1 further including a second supplementary filter which selectively passes the excitation wavelength but blocks at least part of the wavelength interval containing spurious optical signals arising from said first optical fiber and is placed in the optical path between said first collimating lens or lens assembly and said angled primary filter.

5. The optical probe of claim 4 wherein said second supplementary filter is selected from the group comprising a longpass edge filter, a bandpass filter, and a holographic bandpass filter.

6. The optical probe of claim 1 further including both said first and said second supplementary filters.

7. The optical probe of claim 1 wherein said second reflecting element is a prism.

8. The optical probe of claim 1 wherein said second reflecting element is a mirror.

9. An optical probe useful for conducting Raman spectroscopy remotely over optical fibers with minimal interference from Raman scattering and or luminescence within said fibers comprising
    a first optical fiber transmissive at the wavelength used for Raman excitation for transmitting the Raman excitation light to the sample
    a probe head assembly of optical elements said assembly having the functions of delivering light from the end of said first optical fiber to the sample, of collecting Raman scattered light from the sample and of focusing said Raman scattering light into a second optical fiber
    said second optical fiber transmitting said Raman scattering light to a detector means for measuring the intensity and or spectral distribution of said Raman scattered light
    said probe head optical assembly also having the geometric configuration such that the input and output fibers are colinear and are connected to the proximal end of the probe and the sample is illuminated from the distal end of the probe head wherein
    said probe head assembly comprising
    a first lens or lens assembly spaced from the exit of said first optical fiber for collimating the light exiting said first optical fiber, followed in the optical path by
    a primary optical filter that is tuned to pass said Raman excitation wavelengths, but that is rejecting of light of other wavelengths generated within said first optical fiber by said excitation light
    said primary optical filter being arranged at approximately 45° with respect to the light path, followed in the optical path by
    a second lens or lens assembly for focusing the light
    said second lens or lens assembly directing the Raman excitation light onto the sample
    the scattered light from the sample being collected and collimated by the same second lens or lens assembly used for focusing the exciting light
    said collimated scattered light impinging onto the back face of said angled primary optical filter followed in the optical path by
    a second filter in a spaced parallel arrangement to said first filter and with a similar optical property, so that one or more internal reflections of the Raman scattered light occurs between the said two filters, the final reflection off said second filter directing the light onto a third lens or lens assembly
    said third lens or lens assembly focusing said reflected light into the end aperture of said second optical fiber or fiber bundle, approximately parallel to said first optical fiber or fiber bundle and transmissive at the wavelength of the Raman scattered light
    said second optical fiber transmitting said Raman scattering light to a detector means for measuring the intensity and or spectral distribution of said Raman scattered light.

10. The optical probe of claim 1 or 9 wherein said sample is confined to a substrate which is electrically conductive and incorporated into an electrochemical cell.

11. The optical probe of claim 1 or 9 wherein said sample is confined to a substrate which is attached to a heater for controlling the adsorption and desorption of the sample.

12. The optical probe of claim 1 or 9 wherein said second lens or lens assembly focuses the light into a secondary optical fiber
    said secondary optical fiber being used to probe a high temperature environment.

13. A Raman spectrometer utilizing the optical probe of claims 1 or 9 wherein laser lights is coupled into the first optical fiber, is directed onto the sample via the probe head assembly, the Raman scattered light being collected by the same said probe head assembly, said scattered light being directed into a second optical fiber or fiber bundle within said probe, said second optical fiber or fiber bundle extending from the probe to a spectrometer comprising a monochrometer or interferometer and a detector.

* * * * *